Figure 3:
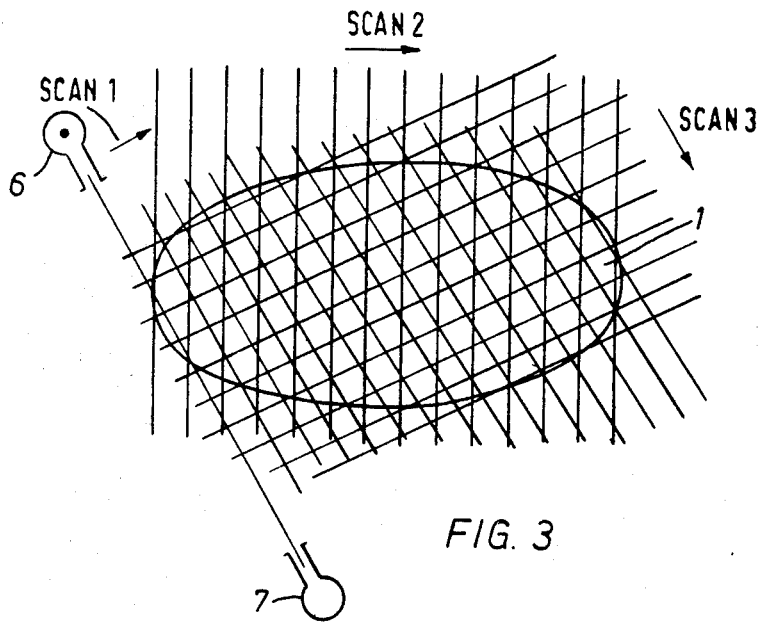

United States Patent [19]
Hounsfield

[11] 3,944,833
[45] Mar. 16, 1976

[54] APPARATUS FOR EXAMINING A BODY BY RADIATION SUCH AS X OR GAMMA RADIATION

[75] Inventor: Godfrey Newbold Hounsfield, Newark, England

[73] Assignee: E M I Limited, Hayes, England

[22] Filed: May 7, 1974

[21] Appl. No.: 468,005

Related U.S. Application Data

[60] Division of Ser. No. 349,198, April 9, 1973, Pat. No. 3,866,047, which is a continuation-in-part of Ser. No. 212,778, Dec. 27, 1971, Pat. No. 3,778,614, which is a continuation of Ser. No. 861,538, Aug. 21, 1969, abandoned.

[30] Foreign Application Priority Data
Aug. 23, 1968 United Kingdom............... 40317/68

[52] U.S. Cl. ................. 250/367; 250/360; 250/490
[51] Int. Cl.² ........................................... G01T 1/20
[58] Field of Search ........... 250/360, 358, 492, 366, 250/367, 312, 320, 321, 490

[56] References Cited
UNITED STATES PATENTS

| | | | |
|---|---|---|---|
| 2,110,954 | 3/1938 | Grossmann | 250/490 |
| 2,528,521 | 11/1950 | Kaiser | 250/360 |
| 3,499,146 | 3/1970 | Richards | 250/490 |
| 3,835,323 | 9/1974 | Kahil | 250/494 |

*Primary Examiner*—Harold A. Dixon
*Attorney, Agent, or Firm*—Fleit & Jacobson

[57] ABSTRACT

Apparatus for examining a body by means of radiation such as X or γ radiation includes a source of a substantially planar, sectoral-shaped swath of said radiation, collimator means having a plurality of apertures formed therein through which respective finger-like beams of the radiation can pass. The beams follow respective linear paths through a region of interest and toward detector means located on the opposite side of said region to the source; the detector means including a respective detector device for each of said finger-like beams. Conveniently each device consitutes a scintillator device and an associated photomultiplier tube, and the tubes associated with adjacent scintillator devices are misaligned to accommodate their widths. Means are also provided for orbiting the apparatus relative to said region of interest.

2 Claims, 24 Drawing Figures

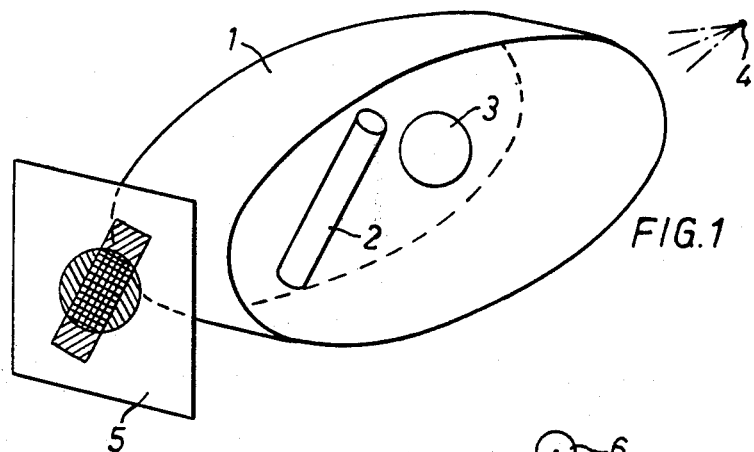
FIG.1
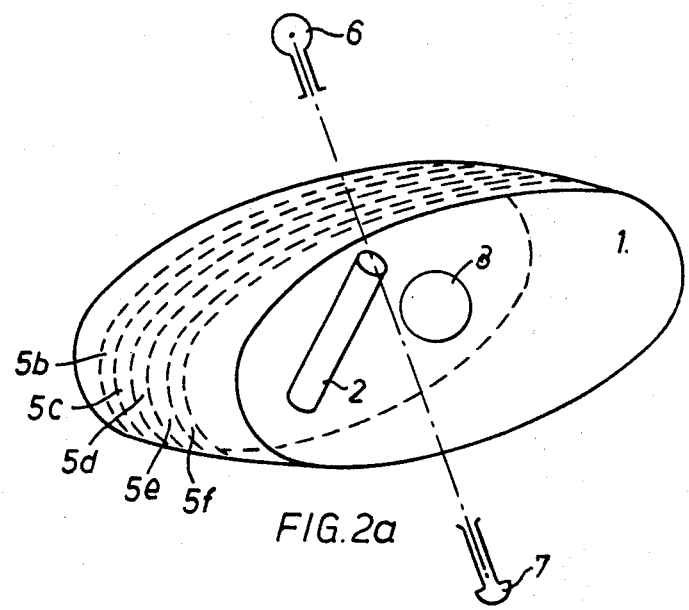
FIG.2a
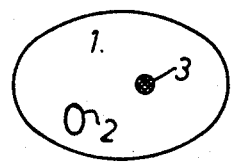 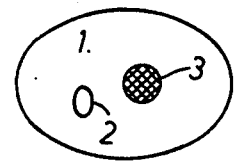 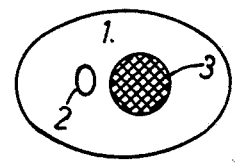
FIG.2b   FIG.2c   FIG.2d
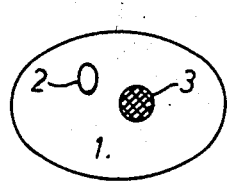 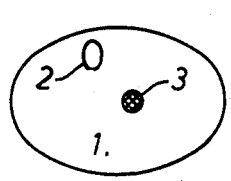
FIG.2e   FIG.2f

APPARATUS FOR EXAMINING A BODY BY RADIATION SUCH AS X OR GAMMA RADIATION

This application is a divisional of my application Ser. No. 349,198, filed Apr. 9, 1973, now U.S. Pat. No. 3,866,047 which is a continuation-in-part of my application Ser. No. 212,778, filed Dec. 27, 1971 (now U.S. Pat. No. 3,778,614 issued Dec. 11, 1973), which is a continuation of my application Ser. No. 861,538, filed Aug. 21, 1969 (now abandoned). The present invention relates to a method of, and apparatus for examining a body by means of radiation such as X or $\gamma$ radiation.

The method and apparatus according to the invention can be used to produce radiographs in any convenient form, such as a picture on a cathode ray tube or other image forming device, a photograph of such a picture, or a map of absorption coefficients such as may be produced by a digital computer and on which "contours" may subsequently be drawn.

One object of the present invention is to provide apparatus for examining a sectional slice of a body by means of penetrating radiation in such a way that information can be obtained from a plurality of sets of rays following ray paths in said slice, the rays in one set being angularly spaced from those in another.

Another object of the present invention is to provide apparatus for examining a sectional slice of a body by means of finger-like beams of penetrating radiation which are defined by collimator means from a substantially planar, sectoral-shaped swath of the radiation.

Another object of the invention is to provide an improved method of, and apparatus for, examining a body by means of penetrating radiation, and in which substantially no relative motion is required between a source of radiation and one or more radiation detectors.

Another object of the present invention is to provide an improved method of, and apparatus for, examining a body by means of penetrating radiation, whereby the examination can be carried out rapidly.

Yet another object of the present invention is to provide apparatus for examining a sectional slice of a body by means of finger-like beams of penetrating radiation which are defined by collimator means from a substantially planar, sectoral-shaped swath of the radiation, wherein a respective detecting device is provided for each said beam and each device comprises, in combination, a scintillator material and a photomultiplier tube; the tubes being of larger dimensions laterally than the scintillators, and wherein adjacent tubes are misaligned to accommodate said dimensions.

Figure 4:
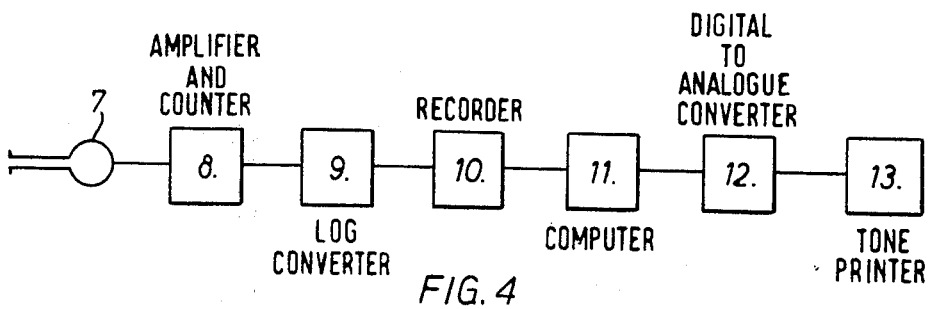
Figure 5:
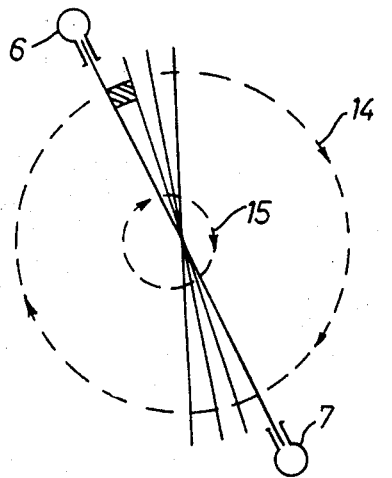
Figure 6A:
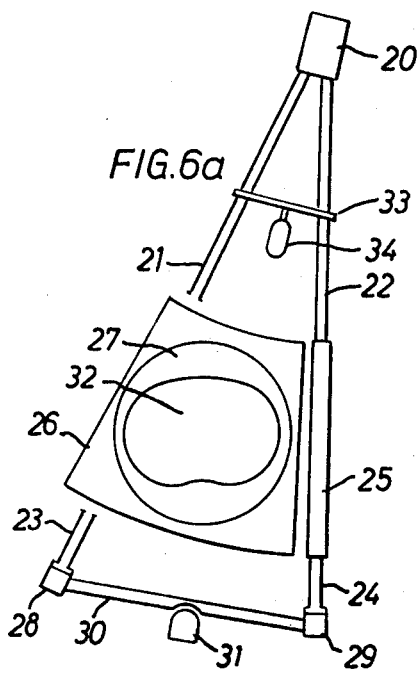
Figure 7:
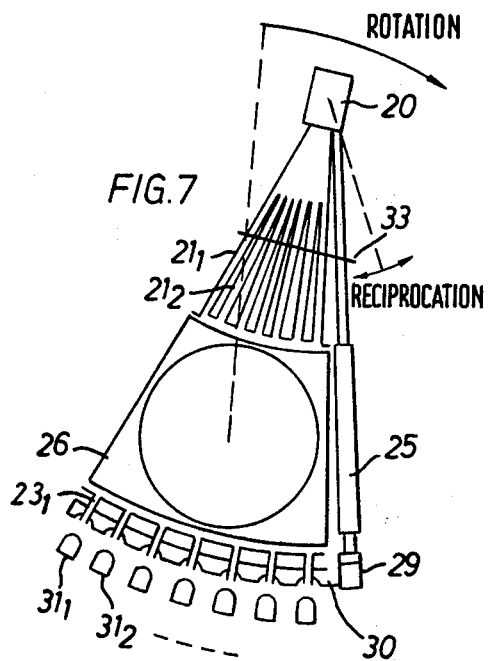
Figure 8A:
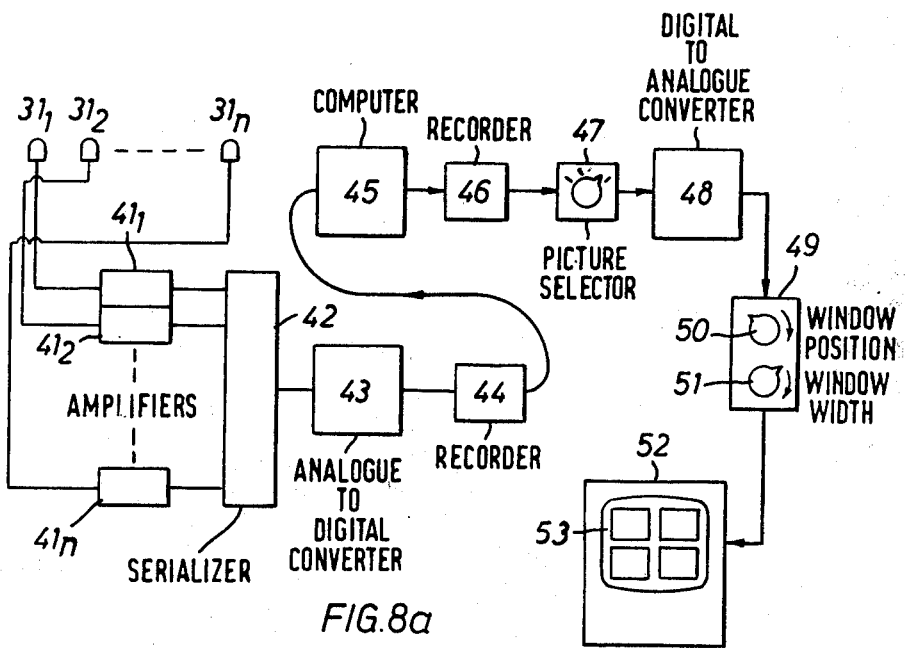
Figure 6B:
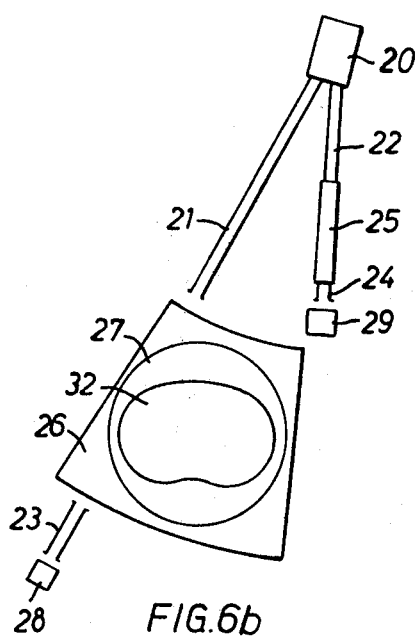
Figure 10:
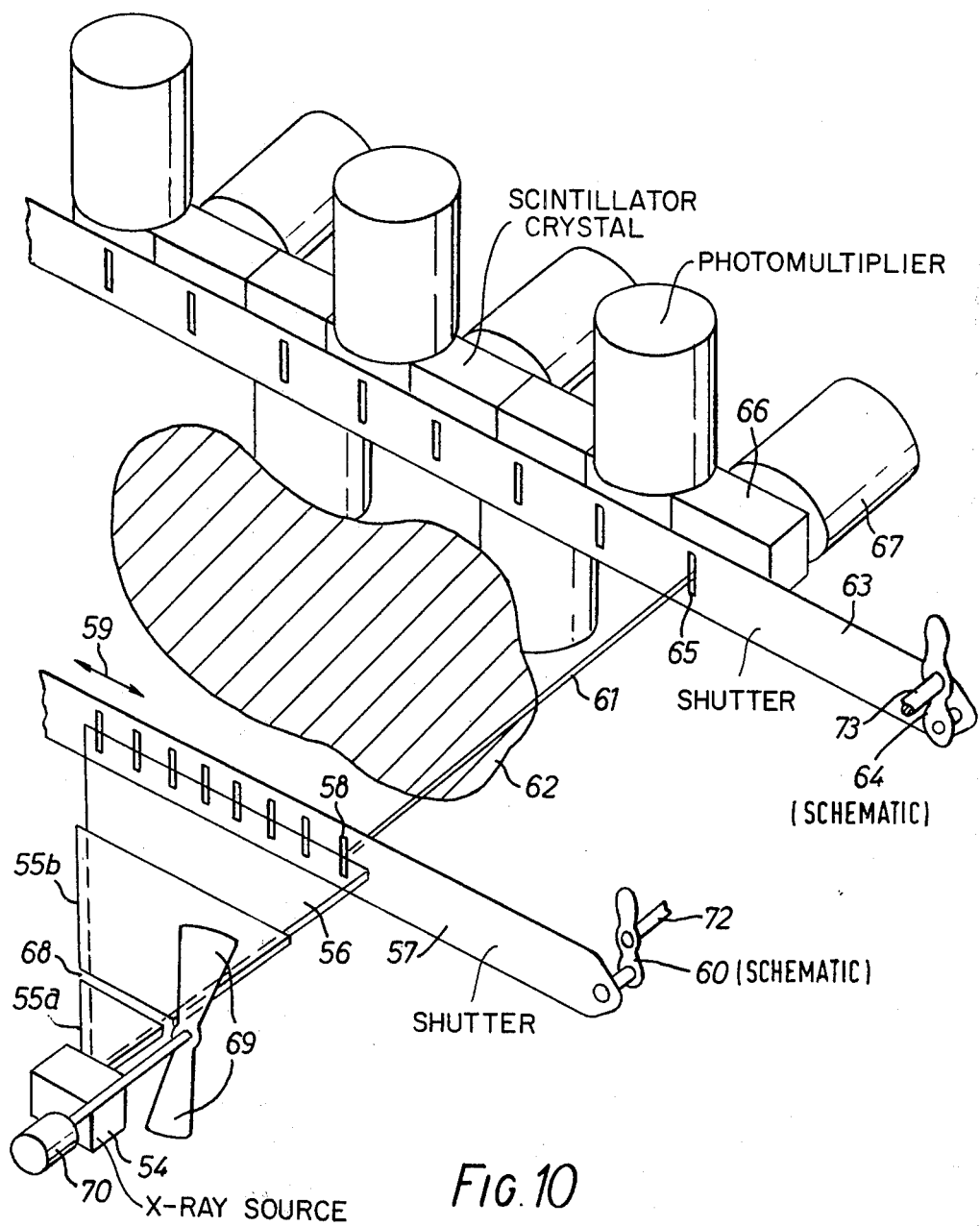
Figure 11:
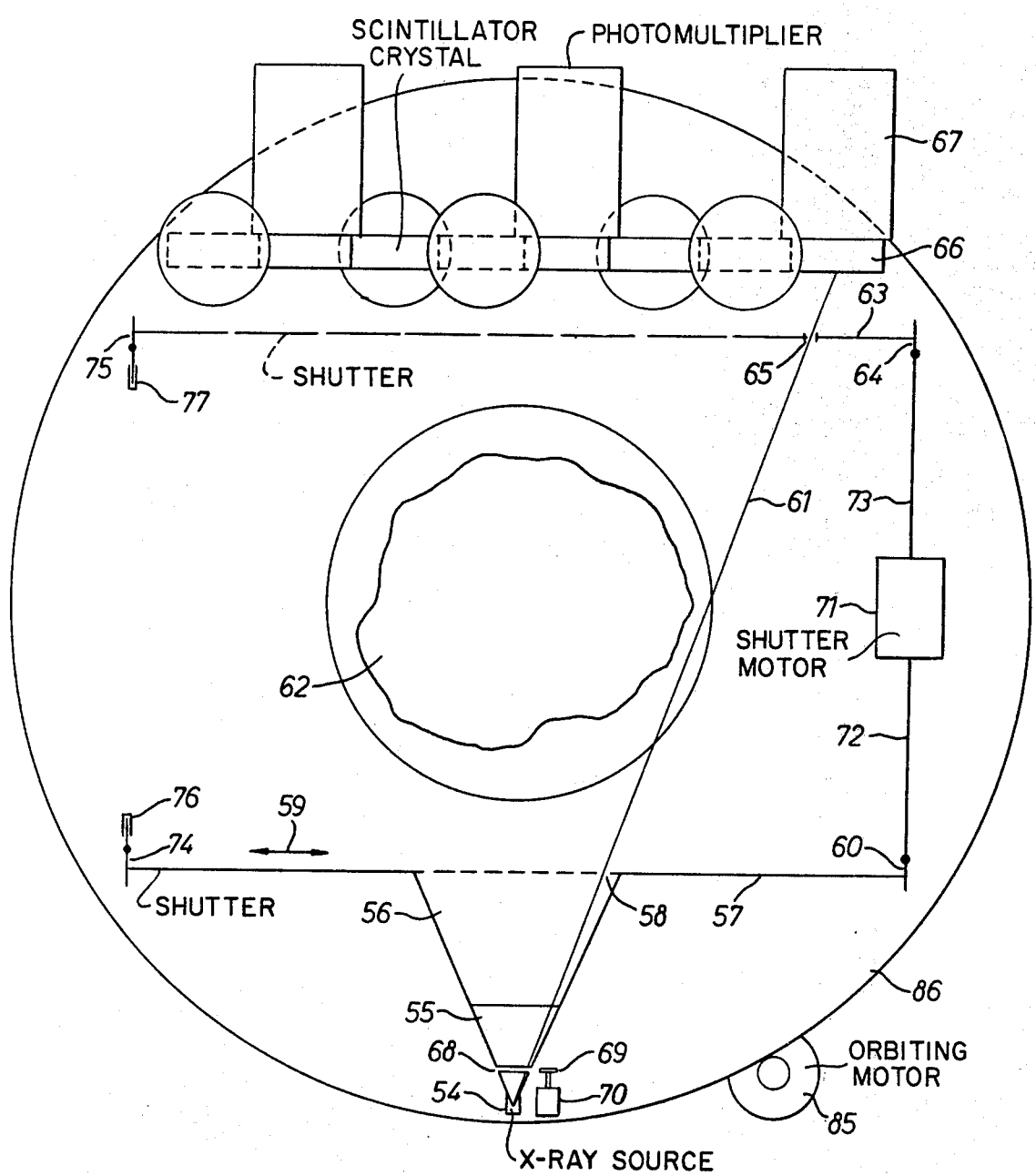
Figure 12:
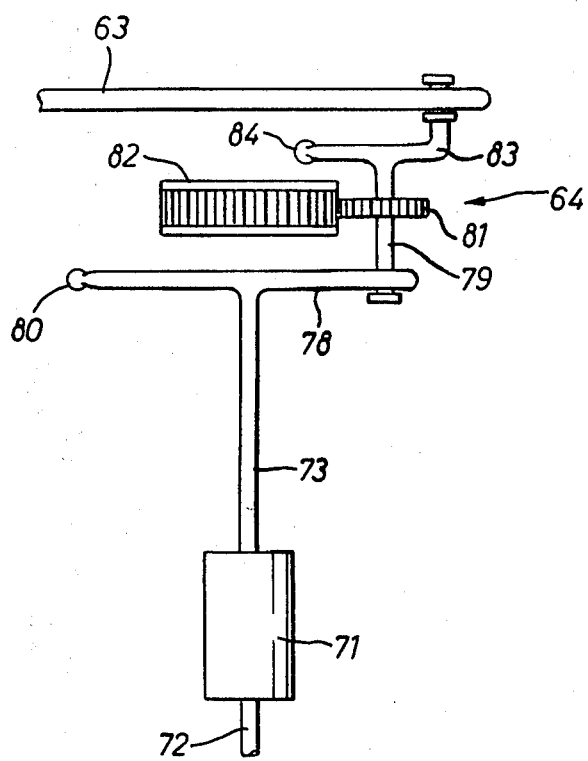

In order that the invention may be clearly understood and readily carried into effect, the same will now be described with reference to the accompanying drawings in which:

FIG. 1 shows the kind of picture produced by conventional X-ray apparatus,

FIGS. 2a, 2b, 2c, 2d, 2e, and 2f illustrate the principle of the technique claimed in my application Ser. No. 212,778 and the kind of picture produced by said technique, FIG. 3 shows one method of scanning used in the said technique, FIG. 4 shows in block form suitable apparatus for carrying out the said technique, FIG. 5 shows an alternative method of scanning, FIGS. 6a and 6b illustrate diagrammatically the construction of the scanning means of apparatus according to two other examples of the said technique, FIG. 7 illustrates a modification of FIG. 6a, which constitutes a first example of my present invention, FIG. 8a illustrates, partly in block form, the apparatus embodying the scanning means illustrated in FIG. 7, FIGS. 8b 8c and 8d are diagrams useful in explaining the operation of parts of the apparatus shown in FIG. 8a, FIGS. 9a, 9b, 9c and 9d illustrate the application of weighting factors to elements of the picture, FIG. 10 shows, in perspective view, apparatus according to another example of my invention, FIG. 11 shows the apparatus of FIG. 10 in plan view, and FIG. 12 shows in some detail part of an arrangement for driving the shutter members shown in FIGS. 10 and 11.

Referring to FIG. 1, this shows a body 1 containing a bone 2 and a tumour 3. Also shown are a source of X-rays 4 and an X-ray film 5. As can be seen, images of the bone and tumour are produced on the film, but partly superimposed. The tone of any point on the film is dependent on the product of the co-efficients of transmission of all the elements lying between that point and the X-ray source. Thus if the bone 2 has the lowest co-efficient of transmission, the tumour 3 the second lowest and the surrounding material the highest, the X-ray image comprises a dark patch where the bone and tumour are superimposed, a lighter patch due to the bone not superimposed on the tumour and a still lighter patch due to the tumour not superimposed on the bone. These are surrounded by a light area where neither bone nor tumour is present. Also as the differences between the co-efficients of transmission of tumour and normal tissue are small, the differences in tone between the different parts of the X-ray picture are slight and difficult to detect using such a method.

Referring now to FIG. 2, the body, bone and tumour are denoted by the same references as in FIG. 1. The X-ray source is replaced by a source 6 which may also be of gamma rays but is preferably of X-rays. It differs from source 4 in that it produces a beam of small cross section area or a ray as it might also be called, for example 3mm. square or diameter, and preferably includes a collimator to reduce scatter of the rays. The X-ray film 5 has been replaced by a detector 7, which may be a scintillator and a scintillation counter and which preferably also includes a collimator. The body 1 is scanned by the beam in one plane only, the plane being 3mm. thick in this example, in a direction not only linearly across the plane, but at a plurality of angles round the plane, the detector 7 being so mounted that it is always pointing towards the source 6. FIG. 3 illustrates the scanning in more detail. If only a single scan across the plane were performed, the result would merely be equivalent to a conventional X-ray picture of that plane, all the objects on a line between source 6 and detector 7 being superimposed. However by performing a large number of scans, sufficient information can be derived to enable the coefficient of absorption of the material in such 3 mm. cube of material in the plane to be calculated and the co-ordinates of its position in the plane determined. Although only three scans are shown in FIG. 3 it will be appreciated that many more would be required in practice.

In each position of the beam the detector 7 determines the transmission of the X radiation by a path of relatively small cross-sectional area through the body. The plane under examination is regarded as a two dimensional matrix of elements and the directions and numbers of the paths is such that each element of the matrix is intersected by a group of paths, which paths intersect different groups of elements.

From the transmissions by all the paths, a series of simultaneous equations is built up represented by the discrete output signals, derived from the radiation traversing all the respective paths and by means of a digital computer provides the absorption coefficient of each element of the matrix. The outputs of the computer may be used to produce a picture or other representation of the section in any convenient form. Successive parallel planes may be examined in this way, and a picture of each planar slice produced to build up a picture of the entire body or a larger section of it. The slices may be examined in sequence or simultaneously by using a number of X-ray sources and detectors in parallel. FIGS. 2$b$ to 2$f$ show the pictures resulting from examination of planar slices 5$b$ to 5$f$ of body 1.

FIG. 4 shows a block diagram of the apparatus for producing pictures from the outputs from detector 7. The output from detector 7 is applied to an amplifier and counter 8 which produces a digital output representing the number of counts in each reading. The output from 8 is converted to logarithmic form in a logarithmic converter 9 whose output is stored in a punched-tape or magnetic tape recorder 10 before being transmitted to a digital computer 11 for processing. The computer 11 produces for each 3 mm. cube of a planar slice of body 1 a digital number representing the absorption coefficient of the material within that cube. These digital numbers may be converted to analogue form in digital-to-analogue converter 12 and applied to a tone printer 13 to produce a picture. Alternatively, the computer outputs may be retained in digital form for comparison by pattern recognition techniques with other digitised pictures.

To achieve the required result, the absorption along each path is deduced form the transmission by each path and a knowledge of the initial intensity of the beam or ray entering each path. The logarithmic converter 9 is used to provide a linear output so that the total absorption along a path is equal to the sum of the absorption in each small element along the path. Let 100 parallel paths be used for each of 400 directions spaced equally over 180°. The computer 11 has then 40,000 figures to process, each representing the total absorption along a given path. Consider the section divided into 100 × 100 similar meshes as on Cartesian graph paper. Each mesh represents an element of the body, but the term mesh will be used in the following mathematical consideration for convenience. The computer 11 is then programmed to give the absorption for each of the 10,000 meshes.

Consider a ray which passes through a set of $n = 100$ meshes through none of which a ray has previously passed. Let the total absorption be Z dB. The computer then allocates a provisional value of Z/100 to each of the meshes. Now suppose that, at a later stage, a ray passes through another set of 100 meshes the absorption in some or all of these meshes having already been allocated. Let the sum of the figures already allocated be $Z_1$ whereas the new measurement gives a total absorption $Z_2$. It will be appreciated that $Z_1$ constitutes a reconstruction of the output signal $Z_2$ derived from the last approximations to the absorptions of the respective meshes. Then a correction $(Z_2 - Z_1)/100$ is added to the figures already appearing in each of the meshes. This process is then continued for all the 40,000 rays. This process gives a rough approximation, but to obtain better accuracy, the computer must repeat it a number of times, say 5.

Consider a single section of the body in the xy-plane in which the absorption per unit distance in dB at the point $x$, $y$, is $z$:

Let $z = f(x,y)$.

Now consider a single set of rays all parallel to the y-axis and spaced equally by intervals $\Delta x$. The rays are arranged to have a width rather greater than $\Delta x$ so that some overlapping occurs. The optimum beam width is determined empirically. For mathematical purposes the change of absorption through any interval $\Delta x$ is assumed to be negligible. We now suppose that the section of the body to be examined is bounded on two sides by the x- and y-axes and is square in shape so that it can be divided into M elementary squares with edges parallel to the axes.

The complete total of rays can be divided into sets each of which consists of parallel rays or effectively parallel rays at a given angle or mean angle. The sets of discrete output signals derived from the rays in each set are treated in the computer in sequence. However, since there are only about 100 × 100 meshes and about 400 angles are employed within 180°, rays at neighbouring angles must include some of the same squares and their absorption will not, therefore, be independent. If the sets were therefore taken in angular succession the lack of independence would clearly lead to a slower convergence than if they were independent.

The computer is therefore arranged, by programming, to take the different angular subsets in a pseudo random order with large angular gaps, of say 40°, between successive sets of rays. The sequence is intended to ensure that every angle is included, but not repeated, within the 400 directions. Rays close together in angle then appear far apart in the computer scanning sequence.

The accuracy of detection by detectors such as 7 is limited so that the raw data contain errors and therefore, as the complete cycle of 100 × 400 measurements is analysed 4 or 5 times by the computer, the resultant figures for the meshes tend to oscillate. It has been found that this can be avoided by multiplying the later corrections by a factor which is less than unity and falls steadily for successive cycles.

The procedure may be represented mathematically as follows. The true continuous distribution function is given by equation (1)

$$z = f(x,y) \qquad 1$$

Let the distribution function reached at some stage of the work be $$z' = g(x,y) \qquad 2$$

which is a discontinuous function since $z'$ must have the same value over each mesh.

Now consider an arbitrary ray passing through $n$ meshes. If $z_r$ is the mean value of $z$ through the $r$th mesh and Z is the total absorption (or attenuation) of the ray in dB as measured $$Z = \sum_{1}^{n} z_r \qquad (3)$$

The value of $z'$ for each mesh will also be known from the previous work. If no ray has passed through a given mesh $z'$ is put equal to zero.

The mean square error for all the meshes along the path of the ray will be written E where $$nE = \sum_{1}^{n} (z_r' - z_r)^2 \qquad (4)$$

and it is required to choose new values $z_r''$ to replace $z_r'$ in order to minimise E.

There is no reason to favour one mesh rather than another, and therefore a constant C is added to $z_r'$ where C is independent or $r$ and must be obtained from the additional information provided by Z. Hence $$z_r'' = z_r' + C \qquad 5$$

Hence the new value of $n$ E will be $$nE = \sum_{1}^{n} (z_r'' - z_r)^2 = \sum_{1}^{n} (z_r' - z_r + C)^2 \qquad (6)$$

The minimum value of E is obtained where C is equal to the mean value of $z_r - z_r'$ or $$C = \frac{\sum_{1}^{n}(z_r - z_r')}{n} = Z/n - \frac{\sum_{1}^{n} z'_r}{n} \qquad (7)$$

Hence $$z_r'' = z_r' + Z/n - \frac{\sum_{1}^{n} z_r'}{n} \qquad (8)$$

In other words the correction applied is equal to the mean value of the error. If none of the $n$ meshes has previously appeared all the $z_r'$ are put equal to zero so that $$z_r'' = Z/n \qquad 9$$

In other words the attenuation is, at first, uniformly distributed among the meshes.

For the $s$th ray equation (8) becomes $$z_{rs}'' = z_{rs}' + Z_s/n - \frac{\sum_{r=1}^{n} z_{rs}'}{n} \qquad (10)$$

If there is a total of S rays there will be a total of S equations for a complete cycle. If $m$ is the number of rays in a set of parallel rays and N is the number of angles $$S = mN \qquad 11$$

If $q$ is the number of complete cycles used by the computer, the total number of ray operations is $q$ S.

Since the number of rays S per cycle is several times the number of meshes M, the number S of equations will be several times the number M of independent equations.

Difficulties arise in finding a system which traces through the picture matrix an equivalent beam or ray as it has been called heretofore which has effectively constant width, and which also includes the correct number of picture elements along its length. Both of these requirements are essential for the accurate computer calculations which are to follow.

Figure 9A:
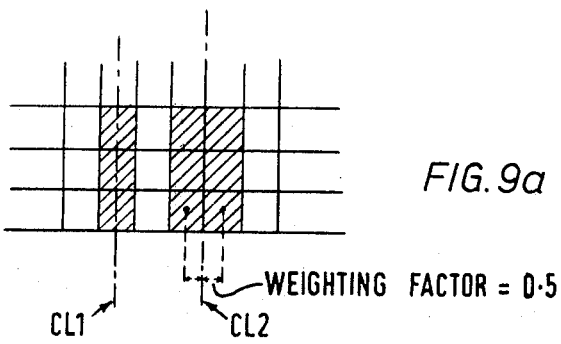

The two worst cases are shown in FIG. 9a, where in one case a beam centre line CL1 passes through the squares of the matrix perpendicularly and the centre line of the beam passes through the centre of the squares, in the other case the beam centre line CL2 passes between the squares. The latter case would add up to twice as many squares as the former, when the squares along the length of the beam are added up, and would clearly give an error of 2:1.

In order to overcome the above problem the values in each square are multiplied by a weighting factor which is a function of the distance from the centre of the square to the centre line of the beam, i.e., the squares of beam 2 in FIG. 9a would have a weighting factor of 0.5, the resulting sum of the numbers in the two beams then being equal.

Figure 9B:
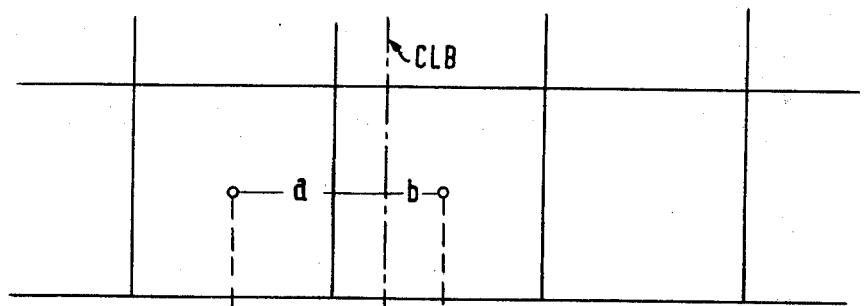

FIG. 9b shows an intermediate position of the beam in which the distances from the centre line CLB of the beam to the centres of the two affected squares in the beam are 'a' and 'b' respectively. The corresponding weighting factors 'A' and 'B' can be read off the graph, and when these are added together they must for reasons indicated above add up to unity. Therefore it follows that the parts of the curves labelled 'x' must be drawn the inverse of the parts labelled 'y', if the beam and hence the weighting curve is to be considered symmetrical about its centre line.

Figure 9C:
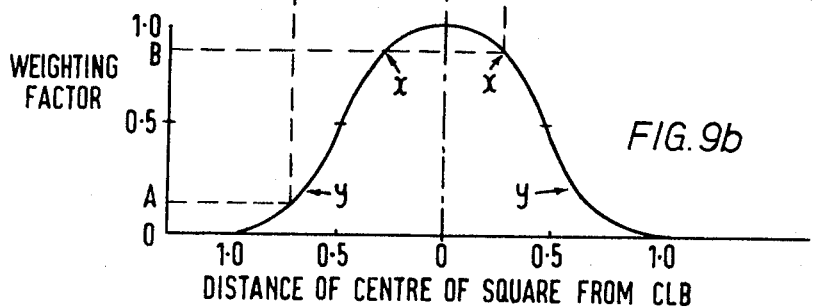
Figure 9D:
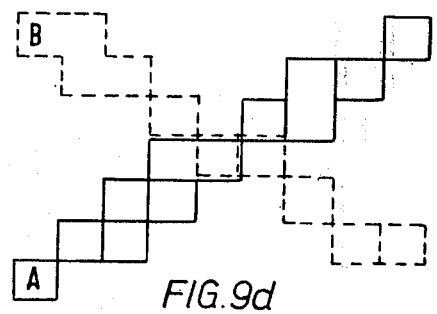

It can be shown that one requirement for accurate summation of values of the matrix squares is idealised in FIG. 9c and its practical equivalent is shown in FIG. 9d using a matrix with a beam at the same angle.

In FIG. 9c the area abcd is obviously constant at any position of the intersection of the beams and is a function of the angle of intersection of the two beams A and B. In FIG. 9d the two equivalent beams vary in width from one to two squares and a constant area at intersection would be impossible without the use of weighting factors. It can be shown that for a given X-ray beam width there is one weighting curve which fulfills all the requirements. For example, if the squares contained at the intersection of the beams in FIG. 9d are multiplied by their respective weighting factors taken from this curve, they will produce a sum which is proportional to the area abcd in FIG. 9c. Any angle of intersection may be chosen and the beam in FIG. 9b may be intersected anywhere along its length for this condition to remain true.

The weighting factor curve can be split up into a table of approximately 20 values to which the computer can refer during calculations without substantially impairing the accuracy of the system.

In the example illustrated in FIG. 3 only a single detector 7 is indicated. If however a fan-shaped or strip beam of radiation is used, with a group of detectors each for receiving radiation transmitted by one of the paths of small cross sectional area, some correction may have to be made in solving the equations for the effect of Compton scatter but in many cases this can be avoided by adequate spacing of the detectors.

As was previously mentioned, the differences in absorption between different materials is very small. However, in accordance with the invention the contrast of the picture produced can be so arranged that the full black to white range represents only the small range of absorption values which is of interest.

It is essential in all X-ray apparatus to ensure that the patient does not receive an overdose of radiation. In this respect the use of a scintillator and a scintillation counter is advantageous as its efficiency and accuracy in detecting X-rays are several orders better than those of photographic film. The maximum detail obtainable in a picture is a function of the number of counts per reading received by the scintillation counter around the edge of the body. In view of the limitation on the permissible number of counts per reading, it would not be feasible to produce a picture having the same order of definition as a television picture when examining a living body, although a high definition picture of an inanimate object could be produced. Moreover, in examining living bodies, it is not normally necessary to have a high definition picture of the whole body. Apparatus according to the invention can be used to produce a picture which is of high definition in the area of immediate interest and of low definition in surrounding areas. For example, as shown in FIG. 5 the radiation source 6 and detector 7 may be arranged to perform a circular scan indicated by the arrow 15 round the edges of the body, which is so positioned that the area of interest is near the centre of the scan. By averaging the number of counts over a small angle of rotation, mean values of absorption for areas enclosed by the angle such as the area shown shaded, may be calculated. It is clear from FIG. 5 that near the edges of the body only a relatively small number of large area elements are being examined, whereas at the centre a large number of small area elements is examined. Consequently the resulting picture will have a high definition near the centre and a low definition towards the edges. In producing the picture, the points may conveniently be plotted in polar co-ordinates. As in the example of FIG. 3, a large number of scans is required to produce sufficient information. In the embodiment of FIG. 5, the additional scans may be produced by superimposing a slower rotary motion which shifts the axis of the main rotation so that the centre of the circle of the main scanning motion traces a circle of small diameter. This additional scanning motion produces the intersecting paths for each element of the matrix according to which the body is examined. The superimposed motion need not be circular and need not be confined to the centre circle. For example it could be a spiral starting at the edge of the outer circle progressing rapidly towards the centre then performing a slow spiral in the region of the centre. It may be more complicated provided that it achieves the object of even coverage at the centre.

Referring to FIG. 6a of the drawing there is represented therein an X-ray tube 20 from which the rays, when the tube is operating, pass through two collimators 21 and 22. The collimator 21 is aligned with a further collimator 23 and the collimator 22 is aligned with a further collimator 24. Between collimator 22 and 24 is located a dummy attenuator 25. There is a gap between the collimators 21 and 23 for the location of the object to be X-rayed and in the example illustrated this gap is occupied by a plastics block 26 having a central aperture 27 for the body to be X-rayed. Two scintillators 28 and 29 are located at the ends of the collimators 23 and 24 respectively and these communicate optically via a light pipe 30 with a photomultiplier 31. A chopper 33 rotatable by an electric motor 34 is arranged to allow beams to pass through the collimators 21 and 22 only alternately to produce scintillations in the scintillators 28 and 29 for detection by the photomultiplier 31. When the apparatus is in use, the collimators 21 to 24, the attenuator 25, the scintillators 28 and 29, the light pipe 30 the photo multiplier 31, the chopper 33 and the motor 34 are oscillated through the angle subtended by the block 26. The apertures of the collimators 21 and 23 define a ray path traversing the body located in the aperture 27 and the oscillator causes this ray path to scan the angular extent of the oscillation. A planar slice of the body is thus exposed to a fan-shaped sweep of rays, radiating from source 20. The X-ray source 20 does not take part in this oscillation because it produces a beam wide enough to span the block 26. However the whole equipment is arranged to rotate or orbit slowly about the body to be examined by X radiation, so that the body is exposed to successive fan-shaped sweeps from different angles. The body is represented by the outline 32.

The use of the scintillator 29 and the attenuator 25 provides a reference for the photo multiplier 31. The material of the attenuator 25 is selected to have similar absorption properties to the body 32 to be examined so that accurate transmission readings may be obtained from the X radiations which pass through this body substantially independent of the X-ray source intensity. The material in the dummy attenuator 25 compensates, to some extent, for the X-ray tube spectrum drift. The space 27 between the body and blocck 26 is filled with a bag containing water so that the beam intensity received by the scintillator 28 is kept as constant as possible as it traverses the body 32, thus reducing the range of the readings which the photo multiplier 31 has to handle. The apparatus may be callibrated initially by inserting a round homogeneous body in the aperture of the block 26. FIG. 6b is a similar system but the chopper is discarded and two separate detectors are used for measuring the sources and readings through the body.

Figure 8B:
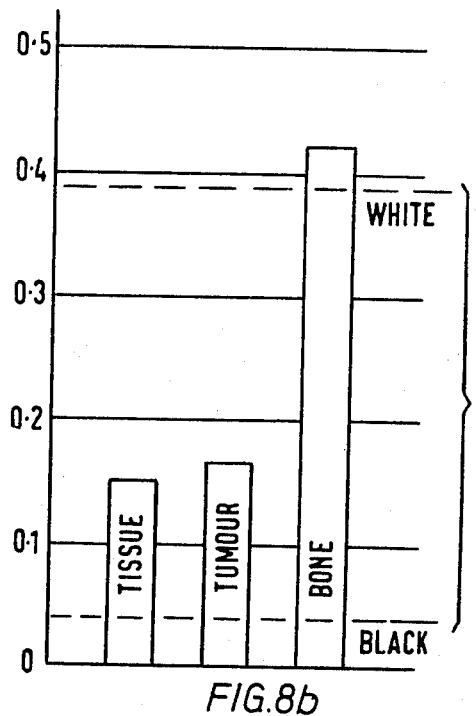
Figure 8C:
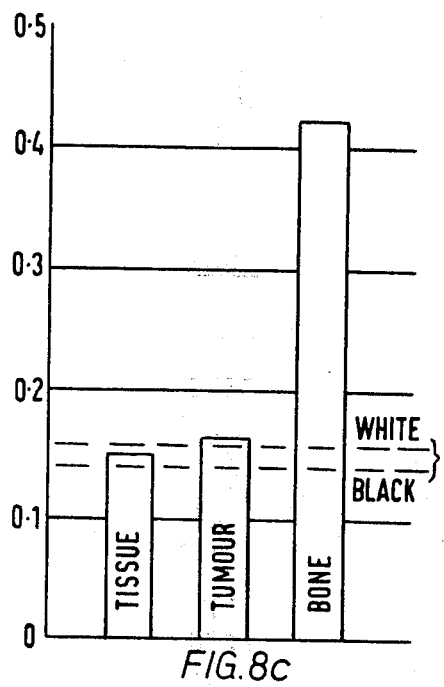
Figure 8D:
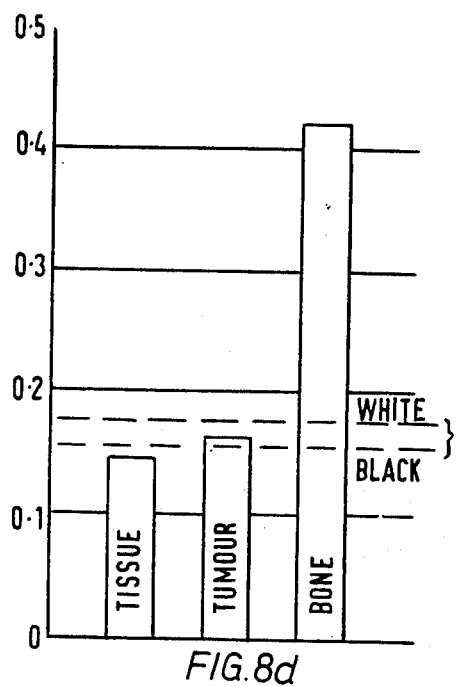

The modification of FIG. 6a which is illustrated in FIG. 7 constitutes one example of my present invention and is intended to reduce the time required to complete an examination. According to this example of my invention, a series of photo multipliers $31_1$, $31_2$ are used instead of the single photo multiplier 31 of FIG. 6. The photo multipliers have a common reference scintillator 29 and light pipe 30. Each photo multiplier has individual collimators between it and the source of X-rays 20, the collimators being denoted by the references $21_1$ and $23_1$ in the case of the photo multiplier $31_1$. With this form of the invention the oscillation of the photo multipliers and the associated collimating systems need be only a fraction of that of the apparatus shown in FIG. 6a, namely that of the sectoral angle between adjacent pairs of collimators. Photo multipliers could also be arranged slightly displaced downwards so that multiple pictures can be taken at one time. As indicated, in FIG. 8a the outputs of the photo multipliers $31_1$, $31_2$ are applied to a series of amplifiers $41_1$, $41_2$ ... and thence to a serialiser 42 which feeds the plurality of outputs of the amplifiers in series to an analogue-to-digital converter 43. The digital output of the converter 43 is fed to a magnetic tape recorder 44 and thence to a digital computer 45 which is programmed to compute the absorption coefficients of the elements of a matrix notionally superimposed in the body 32 under examination. The co-efficients computed by the computer 45 are recorded by a further magnetic tape recorder 46 from which they are applied to a picture selector control device 47. The tape produced by the computer 45 may be replaced on the tape recorder 44, recorder 46 then being unnecessary. The output of device 47 is applied to a digital-to-analogue converter 48 and thence to a control circuit 49 which has a manual knob 50 for controlling the position of the contrast window and another manual knob 51 for controlling the width of the window. The output of the control circuit 49 is fed to a display unit 52 which includes a cathode ray tube having a screen 53. The display unit 52 is arranged to respond to the output signals of the digital computer to build up a visual representation of the section of the object under examination. The term "window" denotes the range of signal amplitudes which is applied to the unit 52 to form the display, and the unit 52 is thus such that different absorption coefficients can be displayed on a scale from black to white. The contrast window width control knob 51 enables the full scale black to white to be occupied by a small or large critical range of absorption coefficients, and the observer may vary the position of the window by manipulation of the control knob 50. FIGS. 8b, 8c and 8d illustrate the effect of varying the width and position of the window. The values of the absorption coefficients are indicated on the vertical scale in these Figures. FIG. 8b illustrates the case in which a wide window is used, that is to say in which the black/white range covers a wide range of values of absorption coefficients. If signals exceeding peak white are removed, for example by limiting, only tissue and tumour will show on the picture. However, as the absorption coefficient of tumour is only 10% greater than that of tissue both will appear as grey and it will be difficult to distinguish between them. FIG. 8c shows the effect of using a narrow window. In this case it is not possible to distinguish between bone and tumour but it is easy to distinguish tissue from both bone and tumour. If signals exceeding peak white are removed, only tissue will show up in the picture.

FIG. 8d shows the effect of altering the position of the narrow window used in FIG. 8c. The tumour now appears as grey while tissue exceeds peak black and bone exceeds peak white. Consequently if signals exceeding peak white and peak black are removed, only the tumour will show up in the picture. It can therefore be seen that by manipulation of the width control knob 51 and position control knob 50 the operator can eliminate from the final picture everything except the material which he wishes to examine. The display unit may also include means for displaying up to four representations of different sections at one time and provision may be made to enable the observer to dwell on one representation. A long after glow tube may be used the picture being replenished by a continuous backwards and forwards pass of the tape deck. The digital computer 45 may be an on line computer and may be remote from the magnetic tape recorders 44 and 46 being connected thereto by suitable lines or the like. Alternatively the magnetic tape recorders may be arranged to store information for computation and display at desired times.

In some cases it may be more convenient to have a direct display. This could employ a cathode ray tube store for storing the data in analogue form. Preferably, the tube should have large values of screen capacity so that the stored information may be interrogated without causing any significant change in its value. Such tubes are commonly used to provide "bright" radar displays. The summation and computing of values received from the cathode ray tube may be carried out by a simple accumulator and comparator operating a serial mode, and the output fed back to the cathode ray tube to give the necessary small additions to the charge built up over the screen. A digital computer would therefore be unnecessary.

In the examples of the invention which have been described, the detecting means detect the transmission of radiation through a plurality of paths which are parallel to the slice being examined. In some cases however some at least of the paths may be oblique to the slice and such oblique paths used to determine the transmission or absorption coefficients of the elements of a three dimensional matrix.

Another example of my invention will now be described with reference to FIGS. 10, 11 and 12 of the accompanying drawings.

Referring now to FIG. 10 the radiation emitted from an X-ray source 54 is formed, by means of a collimator 55, into a fan-shaped (i.e. sectoral) swath 56. The swath 56 is incident upon a first shutter member 57 which is constructed of material opaque to the radiation from source 54. The member 57 is formed with a plurality of slit-like apertures such as 58, only eight such apertures being shown in the drawing for reasons of clarity, although in practice many more apertures are provided. The shutter 57 can be moved to and fro, (i.e. reciprocated) in the direction shown by an arrow 59, by means of a motor driven crank arrangement of which a part is shown at 60 in FIG. 10. The said crank arrangement will be more fully described hereinafter.

The radiation passing through the apertures such as 58 when the shutter member 57 is in a given position constitutes a group of equi-angularly spaced rays; the rays of each group being caused to traverse respective paths such as 61 through a region of interest 62.

A second shutter member 63, which is similar to the member 57, is disposed on the opposite side of the region of interest 62 to the member 57. The member 63 is also moveable (by means of a crank arrangement of which part is shown at 64) in the direction shown by the arrow 59 and its motion is synchronised with that of the member 57 so that apertures such as 65 can be aligned with the apertures such as 58 to form, in effect, a second collimating arrangement for the radiation.

Radiation which passes through a given one of the apertures such as 58 and also through the corresponding aperture such as 65 impinges upon a scintillator crystal such as 66, and the visible energy emitted by the crystal in response to the impinging radiation is collected, amplified, and converted into electrical signals by means of a photo multiplier tube such as 67. The electrical signals are processed substantially as described hereinbefore.

It will be observed that the provision of the pairs of spaced apertures such as 58 and 65 enables the radiation to be scanned, in the direction shown by the arrow 59, over the crystals such as 66. This expedient permits a single crystal/photomultiplier to be used for detecting the radiation passing along a respective ray path through the body which scans the sectoral angle between adjacent ray paths defined by the shutter apertures, so reducing (for a given number of paths and groups of paths) the number of crystals and photomultipliers used.

The positions of the two shutter members 57 and 63 are monitored and these determine the ray path along which radiation impinges at any instant on the crystals. Thus, since the same crystal/photomultiplier combination provides an output signal for radiation passing through the region of interest along several different ray paths, it is necessary that the monitored information concerning the positions of members 57 and 63 be taken into account when the computations described hereinbefore are carried out.

It has been found advantageous to make the dimensions of the crystals such as 66 somewhat less than the total amplitude of scan in the direction of arrow 59 so that, at the extremes of scan, some overlap of the radiation upon an adjacent crystal occurs. This allows an extra reading to be taken in the adjacent crystal/photomultiplier combination so that errors due to the junction line of the two crystals can be compensated for. This expedient also provides information to enable one crystal/photomultiplier combination to be matched to the adjacent combination for gain.

The collimator 55 includes a slit 68 which is parallel to the direction indicated by arrow 59, and a shutter 69 is provided as shown so that its blades (which are opaque to X-radiation) can be rotated, by means of a motor 70, into and out of the slit 68 so as to blank off the X-radiation at the extremity of each stroke of the reciprocating motion of shutters 57 and 63. The motor 70 is synchronised with the reciprocating motion in order to achieve the above end.

In FIG. 11, features which are similar to features of FIG. 10 have been allocated the same reference numerals. In FIG. 11 the crank arrangement for moving the members 57 and 63 in synchronism is shown in schematic form. It may be seen that the parts 60 and 64 are driven from a common motor 71 via respective couplings 72 and 73. At the left hand ends of members 57 and 63 there are provided respective crank parts 74 and 75 which have shafts which are journalled in bearings 76 and 77 respectively. The motor 71 is preferably a 50 Hz synchronous motor.

If the crank arrangement shown in FIG. 11 were used without modification, the to and fro motion of the shutter members 57 and 63 would be substantially sinusoidal, whereas it is desired that they should follow a substantially triangular wave motion. In accordance with a feature of the invention, and as shown in part in FIG. 12, the crank arrangement is modified in a way which introduces third harmonic distortion into the aforementioned sinusoidal motion, so tending to linearise the motion.

Referring now to FIG. 12, the motor 71 drives the shafts 72 and 73 both in the same rotation sense. At the upper end of shaft 73 there is provided a cross-member 78 which is fixed to the shaft 73 to form a T-piece. One end of the cross-member 78 is formed with an aperture (not shown) through which a spindle 79 is passed, the arrangement being such that the spindle 79 can rotate in said aperture. The other end of the cross-member 78 is provided with a balance weight 80.

Fixedly secured to the spindle 79 is a gear wheel 81 which is arranged to be driven around a stationary gear wheel 82 by the action of the T-piece 73, 78. The meshing of the gears on wheels 81 and 82 causes the former wheel to rotate about its own axis, thus causing spindle 79 to rotate. The spindle 79 carries at its upper end a cross-member 83 which is shaped at one end to pass through an aperture in the shutter member 63 and which is provided at its other end with a balance weight 84.

The diameter of the fixed gear wheel 82 is arranged to be twice that of the gear wheel 81 and the arrangement is such that the additional motion imparted to shutter member 63 by virtue of the rotation of gear wheel 81 introduces third harmonic distortion into the substantially sinusoidal motion which would have been produced by T-piece 73, 78 alone and thus linearises the motion of the shutter member.

The drive arrangement for the shutter member 57 can be exactly as shown in FIG. 12 apart from the fact that the dimensions of the cross-members corresponding to 78 and 83 and of the wheels corresponding to 81 and 82 are reduced.

It will be observed from FIGS. 10 and 11 that adjacent ones of the photomutipliers such as 67 are disposed along orthogonal axes. This expedient is used to facilitate the arrangement of the photomultipliers in close proximity to one another, since it will be appreciated that the crystals such as 66 are shown on an enlarged scale and that, in practice, many more than the eight crystals shown are used. It will be appreciated also that a pair of corresponding apertures is provided, one in each of the shutter members 57 and 63, for each crystal such as 66.

Referring again to FIG. 11, the apparatus including the source 54, the first collimator 55, the shutter 69 and its motor 70, the shutter members 57 and 63, the scintillator crystals 66 and the photomultipliers 67 is orbited around the region of interest 62 by means of a motor 85 driving a turntable means 86 on which all of said components are mounted. The motor 85 is preferably synchronised with the reciprocating motion of shutter members 57 and 63 so that each time the shutter members reach an extremity of their travel, the motor 85 is operative to step the turntable around through (say) 1° of rotation. By this means, if all the rays traversing the region 62 at a given angular position of the turntable 86 are referred to as a set of paths, then a corresponding set of paths is traced at each angular position of said turntable. Preferably the turntable is rotated through at least 180° for a given examination.

It will be appreciated that the radiation effects a fan-shaped sweep of the body in a planar slice thereof since the source is a virtual point source in the plane. The source may however have some extent perpendicular to the plane of sweep, since the slice may be relatively thick, or more than one slice may be examined simultaneously. Moreover, in the case where several ray paths are defined by the scanning system, in its rest position, these paths may be parallel, several virtual point sources of radiation then being required.

What I claim is:

1. Apparatus for examining a body by means of penetrating radiation, such as X- or γ - radiation, including source means for producing a substantially planar, sectoral-shaped swath of radiation directed towards the body, the plane of the swath being arranged to define a plane of interest in the body, detector means disposed to receive radiation emergent from the body, the source means and the detector means being disposed on opposite sides of an aperture in which the body can be inserted, collimator means disposed between the source means and the detector means and having a plurality of apertures formed therein through which respective finger-like beams of the radiation can pass such that the beams traverse respective linear paths, in said plane of interest, through the body, said detector means including a respective detector device for each of said beams, each device comprising a scintillator, adapted to scintillate in response to the impact of said radiation, and having a planar output surface through which light can emerge, and a photomultiplier tube having a planar photo-sensitive target juxtaposed with, and substantially parallel to, said output surface; said tube being of larger dimensions, measured in a direction extending across the width of said swath, than said output surface; wherein adjacent scintillators are placed substantially in contact with one another and, in order to adapt the apparatus to accommodate the tubes of adjacent detector devices in said juxtaposed relationship with their respective scintillators, notwithstanding said larger dimensions of said tubes as compared with said scintillators, the output surface of adjacent scintillators are disposed in different planes.

2. Apparatus for examining a body by means of penetrating radiation such a X- or γ- radiation, including source means for producing a substantially planar sectoral shaped swath of the radiation, the plane of the swath being arranged to define a plane of interest in the body, detector means disposed to receive radiation emergent from the body, a locating structure having an aperture in which the body can be inserted, said source means and said detector means being disposed on opposite sides of said structure with said aperture included within the bounds of said swath, collimator means disposed between said source means and said detector means and having a plurality of apertures formed therein through which respective finger-like beams of the radiation can pass such that the beams traverse respective linear paths in said plane of interest through the body, said linear paths being distributed across substantially the full angular extent of said swath, sia detector means including a respective device for each of said beams, and means for orbiting said source means, said detector means, and said collimator means around the body in the plane of said swath.

* * * * *